(12) United States Patent
Reichert

(10) Patent No.: US 6,531,145 B1
(45) Date of Patent: Mar. 11, 2003

(54) ANIMAL ATTRACTANT, REPELLANT AND TRAINING SCENT PRODUCT AND METHOD

(76) Inventor: Tony J. Reichert, 1510 Larkspur La., West Bend, WI (US) 53090

( * ) Notice: Subject to any disclaimer, the term of this patent is extended or adjusted under 35 U.S.C. 154(b) by 0 days.

(21) Appl. No.: 09/607,050

(22) Filed: Jun. 30, 2000

(51) Int. Cl.[7] .............................................. A01N 25/34
(52) U.S. Cl. ..................... 424/408; 424/84; 424/421; 424/724; 424/491; 424/499; 424/545; 424/546; 43/42; 119/905
(58) Field of Search .................... 424/84, 405, 409, 424/421, 490, 491, 499, 545, 546, 724; 119/718, 905; 43/17, 42; 220/560.03, 239, 253

(56) References Cited

U.S. PATENT DOCUMENTS

| | | | | |
|---|---|---|---|---|
| 3,046,192 A | * | 7/1962 | Bilyeu | 424/84 |
| 4,744,374 A | * | 5/1988 | Deffeves et al. | 131/331 |
| 5,888,930 A | * | 3/1999 | Smith | 504/116 |
| 5,970,915 A | * | 10/1999 | Schlueter | 119/171 |

OTHER PUBLICATIONS

Henry Fields Catalog, '97.*
Stokes Seed Catalog, '98.*

* cited by examiner

Primary Examiner—Neil S. Levy
(74) Attorney, Agent, or Firm—Price, Heneveld, Cooper, DeWitt & Litton

(57) ABSTRACT

A method for luring animals, repelling animals and training animals and a product used therewith comprising microporous beads having animal attractant scents, animal repellant scents and animal training scents, respectively, imbibed within the beads. The beads with the animal attractant scents are configured to release the animal attractant scents in order to attract a predetermined animal. Likewise, the beads with the animal repellant scents are configured to release the animal repellant scents in order to repel a predetermined animal. Similarly, the beads with the animal training scents are placed onto a predetermined location and a predetermined animal is trained to perform a predetermined sequence using the beads.

5 Claims, 1 Drawing Sheet

ANIMAL ATTRACTANT, REPELLANT AND TRAINING SCENT PRODUCT AND METHOD

BACKGROUND OF THE INVENTION

The present invention relates to animal attractant scent products, repellant scent products and training scent products.

Heretofore, hunters have lured deer, elk, moose, bear, etc. by spreading liquid attractant scents on the ground near their hunting sites. The animals are attracted to the hunting sites, thereby making hunting of the animals easier. The liquids, however, have typically contained urine and other objectionable products that are unpleasant to have spill on one's clothing. Furthermore, the liquids typically evaporate or sink into the ground quickly.

Repellants in a variety of forms have heretofore been used to repel nuisance animals away from gardens. These often are liquid scents which suffer the same drawbacks. Dogs and other animals have been trained to hunt by applying scents to a drag, and having the dog find the scented drag. Liquid scent is often sprinkled on the ground, a practice which suffers the same drawbacks noted above. Police dogs have been trained to smell illegal drugs by hiding the drugs in certain places and rewarding the dogs when they find the drugs.

SUMMARY OF THE INVENTION

The present invention comprises a method for luring animals, repelling animals and training animals and a product used therewith, comprising microporous beads having animal attractant scents, animal repellant scents and animal training scents, respectively, imbibed within the beads. The scented beads gradually release the scents in order to attract or repel a predetermined animal.

The scented beads are efficient in use, economical to manufacture, capable of a long life, and are particularly adapted for the proposed use.

These and other features, advantages and objects of the present invention will be further understood and appreciated by those skilled in the art by reference to the following specification, claims and appended drawings.

DETAILED DESCRIPTION OF THE PREFERRED EMBODIMENT

For purposes of description herein, it is to be understood that the specific devices and processes illustrated in the attached drawing, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The reference number 10 (FIG. 1) generally designates an animal attractant, repellant and training product of the present invention. The animal attractant, repellant and training product 10 includes microporous beads 12 imbibed with animal attractant, repellant or training scents within the beads 12. The beads 12 gradually release the animal scent in order to attract, repel or train a predetermined animal. Examples of animals one might wish to attract or repel include dogs, deer, bears, squirrels, boars, moose, elk and foxes. Training scents will typically be used to train dogs, for example, to recognize particular bird scents.

The beads 12 of the present invention are preferably made of highly absorbent solid, silica gel which is in granular or particulate form, generally spheroid in configuration, and highly porous. The silica gel is known as microporous silica gel with the granules having a diameter ranging from between about 1 and 10 millimeters. The bulk density of the microporous silica gel is generally between about 400 and 500 grams per liter and the water absorption capacity is at least about 50%, preferably at least about 85%. In order to render the material more highly effective, it is preferably dried to a point where it contains less than about 15% water. This prevents cracking of the individual spherical granules due to moisture content. Such microporous beads are highly absorbent and are commercially available.

Figure 2:
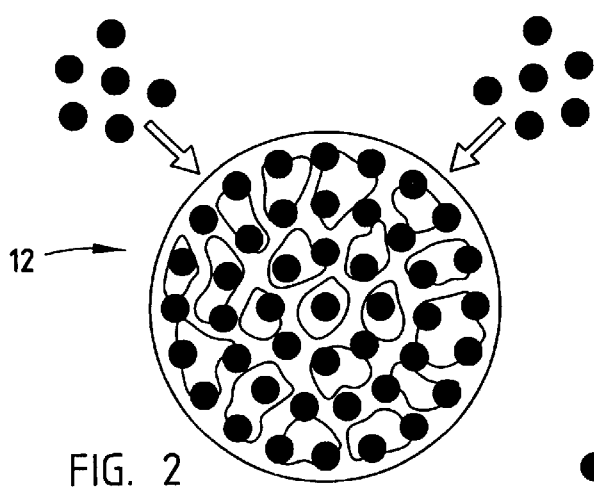
FIG. 2 is a cross-sectional view of a bead during a step of imbibing the bead with a scent of the present invention.

The beads are prepared by first soaking the beads in the appropriate scents (FIG. 2) until the beads are imbibed with the scents. Preferably, the beads are soaked in the animal scents for between fifteen minutes and three hours, and most preferably about one half hour. The scent is provided in liquid form so that it will be imbibed into the beads. The scent may be a liquid, or it may be comprised of a solid in solution. Preferably, the scent is liquid at room temperature, such that the beads can be imbibed at room temperature. However, imbibing at elevated temperatures is possible. Furthermore, the beads are preferably uniformly imbibed with the liquids.

Figure 3:
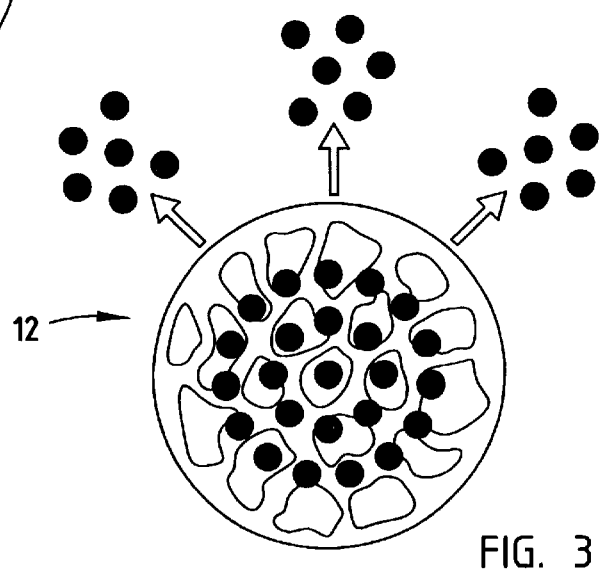
FIG. 3 is a cross-sectional view of the bead during a step of releasing the scent of the present invention.

During use of the beads, the beads will release the appropriate scents through the porous surface of the beads (FIG. 3). It is believed that if the beads are exposed to a natural moisture cycle that can include freezing, thawing and morning dew, the moisture will be absorbed by the beads and assist in releasing more of the appropriate scents from the beads. Therefore, the beads could be used for an extended period of time.

Animal luring scents are defined as any composition that will attract a predetermined animal. For example, the animal luring scents can include a combination of doe urine, hormones and pheromones as sold under the trade name 200 PROOF by Buck Stop Lure Co., Inc. located in Stanton, Mich. The combination of doe urine, hormones and pheromones as described above are used to attract a deer to a predetermined location. Other scents available from Buck Stop Lure Co. include CHARGE II, MULIE DEER, RUCK-n-BUCK, GLAND-U-LURE, RED FOX, NO TRAIL, TRAILMASTER, MATE-TRIKS DOE-IN-HEAT, MOOSE COW-IN-HEAT, BEAR SOW-IN-HEAT, BEAR BATE, TRAPPER'S LURES and UR-N-ALL ANIMAL URINE. The animal luring scents can also comprise tarsal gland secretions of a whitetail buck or urine of a genuine rutting buck. The predetermined animal is defined as any animal that can be attracted by the animal luring scent.

Likewise, animal repellant scents are compositions that will repel a predetermined animal. Animal training scents are defined as any composition that will help train a predetermined animal. The animal training scents are preferably scents that the animal is being trained to recognize.

Figure 1:
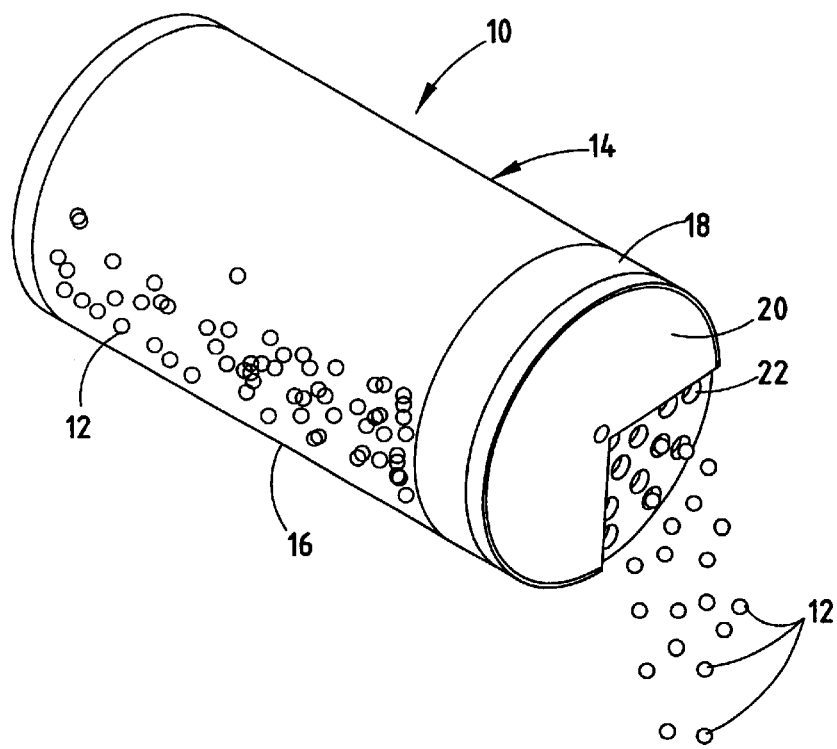
FIG. 1 is a perspective view of a shaker embodying the present invention.

As shown in FIG. 1, beads imbibed with the appropriate scent are preferably placed in a shaker 14. The illustrated shaker 14 is a plastic container 16 with a lid 18. The lid 18 has a rotatable plate 20, whereby openings 22 in the lid 18 can be selectively exposed. The openings 22 are sized to allow the beads 12 to pass through the lid 18 when the plate 20 is rotated and the openings 22 are exposed. The container 16 and the lid 18 seal the inside of the container 16. Therefore, the shaker 14 keeps the appropriate scents within the beads 12 because the beads will not gradually release the scents when the beads are sealed within the shaker 14.

The attractant, repellant and training product 10 is used to lure, repel or simulate for dog training purposes a predetermined animal by first imbibing the beads 12 with the appropriate scent. Thereafter, a location to lure, repel or train is selected. The rotatable plate 20 of the shaker 14 is then rotated and the beads 12 imbibed with the scents are placed onto the location. For attraction, the beads 12 are preferably placed along two converging lines wherein the animal will be influenced or funneled by the animal attractant scents to move towards the converging point of the lines. After the beads 12 have been placed onto the predetermined location, the beads 12 will gradually release the scents into the air.

The above description is considered that of the preferred embodiment only. Modification of the invention will occur to those skilled in the art and to those who make or use the invention. Therefore, it is understood that the embodiment shown in the drawings and described above is merely for illustrative purposes and not intended to limit the scope of the invention, which is defined by the following claims as interpreted according to the principles of patent law, including the doctrine of equivalents.

The invention claimed is:

1. A method of luring animals comprising:
   providing microporous silica gel beads with a diameter of from about 1–10 millimeters, a bulk density from about 400 to 500 grams per liter and a water absorption capacity of at least 50%;
   imbibing the beads with a sufficient amount of animal attractant scent of at least one of urine, hormones and pheromones that attracts a predetermined animal;
   placing the beads onto a predetermined location; and luring the predetermined animal to the predetermined location;
   wherein imbibing occurs before placing, and placing occurs before luring.

2. The method of luring animals of claim 1, wherein:
   imbibing the beads with animal attractant scent includes soaking the beads in the animal attractant scent for about 0.5 hours.

3. The method of luring animals of claim 1, wherein:
   imbibing the beads with animal attractant scent includes soaking the beads in the animal attractant scent between about 15 minutes and about three hours.

4. The method of luring animals of claim 1, wherein:
   the water absorption capacity is at least about 85%.

5. The method of luring animals of claim 1, further comprising:
   providing a shaker with a perforated lid;
   placing the beads within the shaker;
   wherein the step of placing the beads onto the predetermined location includes shaking the beads out of the shaker onto the predetermined location.

* * * * *